United States Patent
Ohishi et al.

(10) Patent No.: US 10,610,537 B2
(45) Date of Patent: Apr. 7, 2020

(54) METHODS OF PRODUCING SIALOOLIGOSACCHARIDES AND USES THEREOF

(71) Applicant: MASAYOSHI LTD., Tokyo (JP)

(72) Inventors: Hifumi Ohishi, Tokyo (JP); Rie Tokuyama, Tokyo (JP); Haruka Arao, Tokyo (JP); Changfang Zhou, Tokyo (JP); Hisanori Tani, Tokyo (JP); Takashi Hattori, Tokyo (JP)

(73) Assignee: MASAYOSHI LTD., Tokyo (JP)

( * ) Notice: Subject to any disclaimer, the term of this patent is extended or adjusted under 35 U.S.C. 154(b) by 0 days.

(21) Appl. No.: 15/683,982

(22) Filed: Aug. 23, 2017

(65) Prior Publication Data

US 2018/0055863 A1 Mar. 1, 2018

(30) Foreign Application Priority Data

Aug. 25, 2016 (JP) .................................. 2016-164565

(51) Int. Cl.
*A61K 31/702* (2006.01)
*C07H 3/06* (2006.01)

(52) U.S. Cl.
CPC ............. *A61K 31/702* (2013.01); *C07H 3/06* (2013.01)

(58) Field of Classification Search
None
See application file for complete search history.

(56) References Cited

U.S. PATENT DOCUMENTS

| | | | | |
|---|---|---|---|---|
| 5,834,423 | A * | 11/1998 | Koketsu | A61K 31/7012 514/2.4 |
| 6,323,008 | B1 * | 11/2001 | Pelletier | C12N 15/8509 435/101 |
| 2004/0039192 | A1 * | 2/2004 | Packer | C07H 1/08 536/123 |
| 2012/0171165 | A1 * | 7/2012 | Buck | A61K 31/702 514/23 |
| 2014/0066617 | A1 | 3/2014 | Chiba et al. | |

FOREIGN PATENT DOCUMENTS

| | | |
|---|---|---|
| JP | H08099988 A | 4/1996 |
| JP | 2002128797 A | 5/2002 |
| JP | 2005008584 A | 1/2005 |
| JP | 2009023926 A | 2/2009 |
| JP | 2011513482 A | 4/2011 |
| JP | 2011-136909 A | 7/2011 |
| WO | 2009113861 A2 | 9/2009 |
| WO | 2012121041 A1 | 9/2012 |

OTHER PUBLICATIONS

Wieruszeski, J. M., Michalski, J. C., Montreuil, J., Strecker, G., Peter-Katalinic, J., Egge, H., . . . (1987). Structure of the monosialyl oligosaccharides derived from salivary gland mucin glycoproteins of the Chinese swiftlet (genus *Collocalia*). Journal of Biological Chemistry, 262(14), 665 (Year: 1987).*

Malicdan et al.,"Prophlatic treatment with sialic acid metabolites precludes the development of myopathic phenotype in the DMRV-hIBM mouse model", Nature Medicine, pp. 690-695, vol. 15 (Jun. 2009).

Noguchi, The role of arginie methylation in the Piwi-interacting RNA pathway, (The Journal of Japanese Biochemistry Society), pp. 316-320, vol. 83 (No. 4) (2012).

Okajima,"Hair-growing effect of a saliva component sialic acid.— the molecular mechanism and possible therapeutic application for alopecia" Fragrance Journal, pp. 43-47, vol. 37 (No. 10) (2009).

Su, H. Y. et al.,"Isulin-like growth factor 1 and hair growth", Dermatol Online Journal, pp. 1-6, vol. 5, No. 1 (1999).

Tavakkol et al.,"Maintenance of human skin in organ culture: role for insulin-like growth factor-1 receptor and epidermal growth factor receptor", Arch Dermatol Res, pp. 643-651, vol. 291 (Mar. 1999).

Nishino et al., Development of therapy for distal myopathy with rimmed vacuoles, Clin Neurol, 2009, vol. 49, No. 11, pp. 852-855. English language abstract on p. 855.

Japanese Office Action dated Jan. 23, 2020, in corresponding Japanese Patent Application No. 2016-164565.

* cited by examiner

*Primary Examiner* — Dale R Miller

(74) *Attorney, Agent, or Firm* — Browdy and Neimark, PLLC

(57) ABSTRACT

The present invention provides a method of producing a sialooligosaccharide, which comprises: (1) hydrolyzing a sialoglycoprotein by heating at a temperature from 70 to 90° C. in an alkaline aqueous solution; and (2) purifying the hydrolysate to obtain the sialooligosaccharide, wherein a weight ratio of sialic acid to hexose contained in the resulting sialooligosaccharide is from 0.5 to 0.9.

4 Claims, 2 Drawing Sheets

(1) Test Substance 2 (treated with hydrogen chloride)

(2) Test Substance 1 (treated with potassium hydroxide)

Changes in the moisture content of skin due to the use of the lotion containing the test substance 1

METHODS OF PRODUCING SIALOOLIGOSACCHARIDES AND USES THEREOF

TECHNICAL FIELD

The present invention relates to methods of producing sialooligosaccharides from raw materials containing sialoglycoproteins, as well as sialooligosaccharides produced by said methods, and hair growth promoting agents and skeletal muscle formation promoting agents comprising said sialooligosaccharides.

BACKGROUND ART

Sialic acids are known to be widely distributed in nature, and are physiologically functioning important substances.

Sialic acids have been reported to possess various functions including intercellular recognition, infection preventing activity, controlling immunological functions, myopathy amelioration, and hair growth or restoration (Non-patent Documents 1-3).

Furthermore, sialic acids are known to promote the production of insulin-like growth factor 1 (IGF-1) (Non-patent Document 3). And IGF-1 is known to have a hair restoring effect (Non-patent Document 4) as well as an action for enhancing skin elasticity (Non-patent Document 5).

In the case of oral administration, the pharmacological/biological activities of sialic acids are known to be such that sialooligosaccharides that are sugar chains containing sialic acids are more active than free sialic acids (Non-patent Documents 1 and 2, as well as Patent Document 1).

A number of methods for producing such sialooligosaccharides have been reported and they include: a method involving purification by organic solvent extraction method and active carbon column chromatography from milk that has been freed of lipids and proteins (Patent Document 2); a method involving purification by ultrafiltration and gel filtration chromatography from milk or a dairy product that has been freed of lipids and proteins (Patent Document 3); a method involving purification from lipid- and protein-free whey by ion exchange resin (Patent Document 4); a method of production from defatted bird egg yolk by extraction with water or a salt solution, or ultrafiltration of a solution obtained by such extraction with water or a salt solution, or enzymatic digestion of a solution resulting from such extraction with water or a salt solution (Patent Document 5); and a method in which cytidine monophosphate-sialic acid is reacted with a sugar chain in the presence of a sialic acid transferase and phosphatase to transfer the sialic acid to the non-reducing terminal of the sugar chain (Patent Document 6).

CITATION LIST

Patent Literature

PTL 1: JP 2002-128797 A
PTL 2: JP 2005-8584 A
PTL 3: JP 2009-23926 A
PTL 4: JP 2011-513482 A
PTL 5: JP H8-99988 A
PTL 6: WO 2012/121041 A1

Non Patent Literature

NPL 1: Malicdan, M C et al., Nat. Med., 15, 690-695 (2009)
NPL 2: Satoru Noguchi, Seikagaku (The Journal of Japanese Biochemistry Society), 83 (4), 316-320 (2012)
NPL 3: Kenji Okajima, Fragrance J., 37 (10), 43-47 (2009)
NPL 4: Su, H. Y. et al., Dermatol, Online J., 5, 1 (1999)
NPL 5: Tavakkol, A. et al., Arch. Dermatol. Res., 291, 643-651 (1999)

SUMMARY OF INVENTION

Technical Problem

All of the aforementioned methods of producing sialooligosaccharides are cumbersome and costly, and are not recognized to give good yields. Furthermore, in the case of performing purification from a deproteinized raw material, glycoproteins containing sialic acids (i.e. sialoglycoproteins) are already removed.

Thus, an object of the present invention is to provide methods of producing sialooligosaccharides from sialoglycoprotein containing raw materials in a simple way, at low cost, and in high yields.

Another object of the present invention is to provide sialooligosaccharides as produced by said methods.

Yet another object of the present invention is to provide hair growth promoting agents and skeletal muscle formation promoting agents that comprise said sialooligosaccharides.

Solution to Problem

The present inventors conducted intensive studies on simple, low-cost, and high-yield methods of producing sialooligosaccharides using raw materials containing mucin-type sialoglycoproteins, and found that sialooligosaccharides can be produced in a simple, low-cost, and high-yield manner by hydrolyzing the nest of a swiftlet with an alkali solution and purifying the resulting hydrolysate, thereby accomplishing the present invention.

Briefly, the present specification encompasses the disclosures of the inventions as set forth below.

[1] A method of producing a sialooligosaccharide, which comprises:
(1) hydrolyzing a sialoglycoprotein by heating at a temperature from 70 to 90° C. in an alkaline aqueous solution; and
(2) purifying the hydrolysate to obtain a sialooligosaccharide wherein a weight ratio of sialic acid to hexose contained in the resulting sialooligosaccharide is from 0.5 to 0.9.
[2] The method according to [1], wherein the sialoglycoprotein is a mucin-type glycoprotein.
[3] The method according to [1] or [2], wherein the sialoglycoprotein is a mucin-type glycoprotein contained in the nest of the Collocaliini tribe.
[4] The method according to any one of [1] to [3], wherein the alkaline aqueous solution is an aqueous solution of potassium hydroxide.
[5] The method according to any one of [1] to [4], wherein the purification is performed by reverse osmosis membrane filtration or electrodialysis.
[6] A sialooligosaccharide, which is produced by a method comprising:
(1) hydrolyzing a sialoglycoprotein by heating at a temperature from 70 to 90° C. in an alkaline aqueous solution; and
(2) purifying the hydrolysate to obtain the sialooligosaccharide wherein a weight ratio of sialic acid to hexose contained in the resulting sialooligosaccharide is from 0.5 to 0.9.
[7] A hair growth promoting agent comprising the sialooligosaccharide according to [6].
[8] A skeletal muscle formation promoting agent comprising the sialooligosaccharide according to [6].

[9] A method for promoting hair growth, which comprises, administering an effective amount of the sialooligosaccharide according to [6] to a subject in need thereof.

[10] A method for promoting skeletal muscle formation, which comprises, administering an effective amount of the sialooligosaccharide according to [6] to a subject in need thereof.

Advantageous Effects of Invention

By means of the methods of producing sialooligosaccharides of the present invention, sialooligosaccharides can be produced from raw materials containing sialoglycoproteins in a simple, low-cost, and high-yield manner Sialic acids are rare ingredients that are extracted from milk, saliva, and the like, and are extremely expensive. Therefore, although their pharmacological actions that affect living bodies are sufficiently understood, sialic acids generally are not used at their physiological concentration (20 mg/kg weight). By virtue of the production methods of the present invention, it has become possible to produce sialooligosaccharides at a cost that enables commercial use at their physiological concentration.

DESCRIPTION OF EMBODIMENTS

Figure 1:
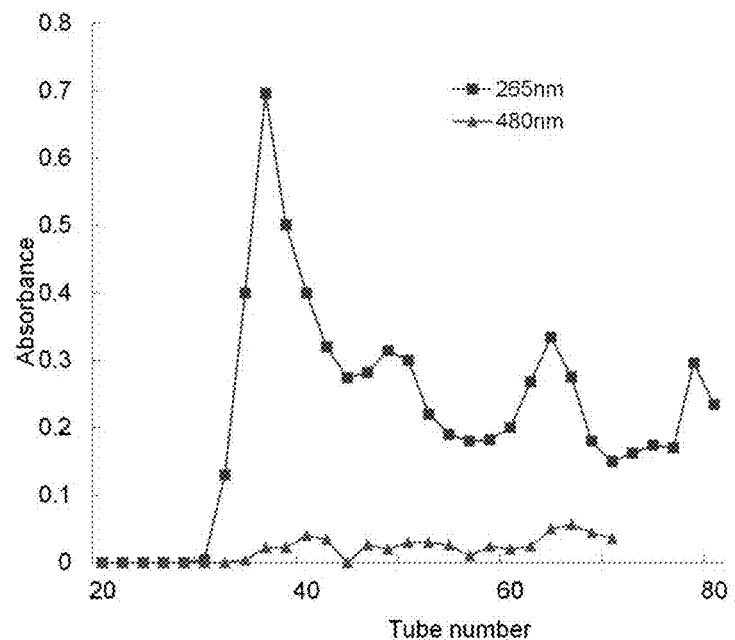
FIG. 1 gives graphs showing the elution patterns of the test substances that were separated by gel filtration chromatography and detected by ultraviolet light absorption at the wave lengths of 265 and 480 nm. (1) shows the elution pattern of the test substance 2 (treated with hydrogen chloride), and (2) shows the elution pattern of the test substance 1 (treated with potassium hydroxide). The vertical axis plots absorbance, and the horizontal axis plots the tube number for each fraction.
Figure 1:
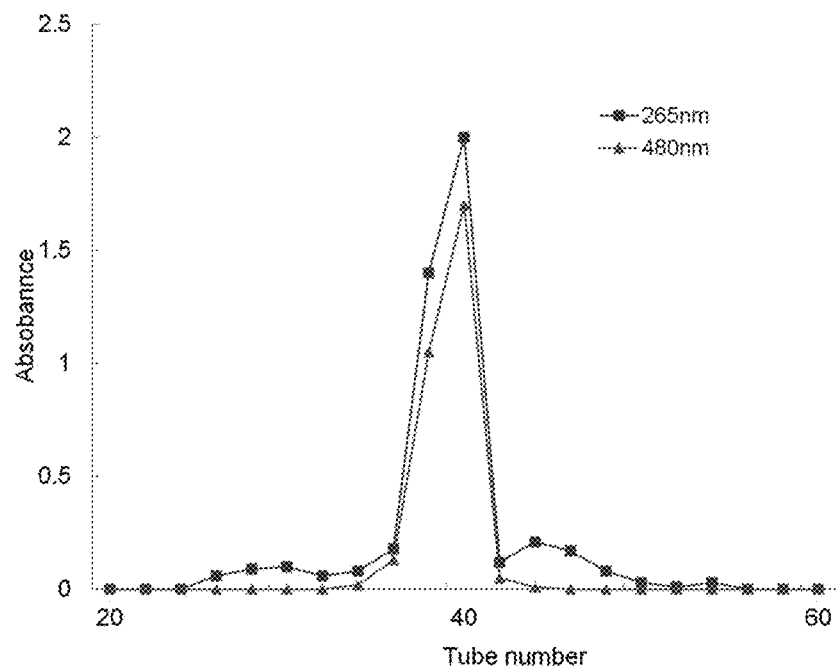

In the present specification, the term "sialoglycoprotein" refers to a glycoprotein containing sialic acids mainly at the non-reducing terminal of its sugar chain.

In the present specification, the term "sialic acid" is a family name that collectively refers to amino or hydroxy group substituted derivatives of neuraminic acid.

In the present specification, the term "hexose" refers to a monosaccharide containing 6 carbon atoms. For example, this term covers allose, altrose, glucose, mannose, gulose, idose, galactose, talose, psicose, fructose, sorbose, tagatose, quinovose, rhamnose, fucose, fuculose, and so forth; the term also covers hexosamines such as glucosamine, mannosamine, galactosamine, and frucutosamine.

In the present specification, the term "sialooligosaccharide" refers to an oligosaccharide containing sialic acids. The sialooligosaccharide of the present invention is composed of hexose monosaccharide units and sialic acid monosaccharide units, and the numbers of the respective monosaccharide units may range from 5 to 10, preferably from 4 to 9. Furthermore, the weight ratio of sialic acids to hexoses contained in the sialooligosaccharide is, for example, from 0.5 to 0.9, and preferably from 0.6 to 0.8.

In general, the known types of sialoglycoproteins in animals are asparagine-type, mucin-type, proteoglycan-type, and others. Sialoglycoproteins to be used for the sialooligosaccharide-producing methods of the present invention may be any of these types.

In the present specification, the term "mucin" refers to a mixture of sugar-rich glycoproteins (mucus glycoproteins) that are contained in the mucus secreted mainly from the epithelial cells of animals.

In the present specification, the term "mucin-type" refers to the mode of binding of a sugar chain to a protein which is found in the glycoproteins of mucin. In this binding mode, the N-acetylgalactosamine of the reducing terminal of a sugar chain is bound mainly to the hydroxyl group of serine or threonine by an α-O-glycoside bond (i.e. mucin-type bond) with high frequency.

The methods of the present invention that produce sialooligosaccharides comprise at least the following steps:
(1) hydrolyzing a sialoglycoprotein by heating in an alkaline aqueous solution; and
(2) purifying the hydrolysate to obtain a sialooligosaccharide.

The sialoglycoprotein to be used for the production of sialooligosaccharide in the present invention may be isolated or may contain any other ingredients. Preferably, such sialoglycoprotein is a mucin that contains a mucin-type sialoglycoprotein.

The sialooligosaccharide produced by the present invention may contain any ingredients other than the sialooligosaccharide.

Examples of alkalis used for the alkaline aqueous solution include potassium hydroxide, sodium hydroxide, and the like.

The concentration of the alkaline aqueous solution is, for example, from 0.01 to 1.0 wt. %, preferably from 0.2 to 0.5 wt. %, and more preferably from 0.25 to 0.5 wt. %.

Heating is performed, for example, at a temperature from 50 to 105° C., preferably at a temperature from 70 to 90° C., and more preferably at a temperature from 75 to 85° C., and lasts, for example, for 30 minutes to 3 hours, preferably for 30 minutes to 2 hours, and more preferably for 1 to 2 hours.

In the present invention, methods for purifying the hydrolysate are not particularly limited.

The purification of the hydrolysate can be performed, for example, by reverse osmosis membrane filtration, dialysis, electrodialysis, or ultrafiltration, preferably by reverse osmosis membrane filtration, dialysis, or electrodialysis, and more preferably by reverse osmosis membrane filtration or electrodialysis.

The purification of the hydrolysate may also be performed by conducting separation and fractionation, for example, with size exclusion chromatography (e.g. gel filtration chromatography, gel permeation chromatography) or reverse phase chromatography, preferably with size exclusion chromatography, and more preferably with gel filtration chromatography.

Furthermore, the purification of the hydrolysate may also be performed by combining the above-mentioned techniques. Moreover, salts and impurities, for example, can be removed by the aforementioned purification process.

In particular, as one mode of the present invention, the hydrolysate is preferably purified by electrodialysis from the standpoint of removing heavy metals and arsenic that may be contained in raw materials.

Furthermore, the purification of the hydrolysate can be performed after removing insoluble matter by appropriate means such as centrifugation or filtration.

Examples of the sialoglycoprotein to be used as a raw material in the production methods of the present invention include sialoglycoprotein-containing substances, as exemplified by naturally occurring substances such as the nests of birds in the Collocaliini tribe, animal milk (e.g. cow's milk), animal eggs (e.g. chicken eggs), saliva or digestive juice of animals (e.g. domestic animals), echinoderm (e.g. sea cucumber), cnidarian (e.g. jelly fish), etc., and, preferably said sialoglycoprotein is a mucin-containing substance.

The nests of birds in the Collocaliini tribe have been eaten as luxury medicinal dishes in Chinese food, etc. since ancient times. Due to the recent boom of health enhancement, ready-to-eat commercial products, extracts, and the like of said nests are commercially available. However, due to the lack of sufficient quality control, commercial products containing high concentrations of heavy metals or arsenic are being distributed. In a preferable mode of the present invention, sialooligosaccharides are produced from which raw material derived heavy metals or arsenic have been removed by the purification process to less than the detection limit.

Sialoglycoproteins contained in the nests of birds in the Collocaliini tribe are mucin-type glycoproteins.

In the case where a sialooligosaccharide is obtained from a sialoglycoprotein contained in the mucin of the nest of a bird in the Collocaliini tribe, sialic acids may be eliminated from the oligosaccharide under an acidic condition, so hydrolysis is performed under a dilute alkaline, mild condition. The methods of the present invention can also be applied in the case where sialooligosaccharides are obtained from other mucin-type sialoglycoproteins. Therefore, the raw materials for sialooligosaccharides are not limited to the nests of birds in the Collocaliini tribe.

The sialooligosaccharide produced by the present invention may be used as a pharmaceutical product, quasi-drug, health food, or cosmetic, etc. For example, said sialooligosaccharide can be used as: solid preparations such as tablets, capsules (e.g. soft-shelled capsules, hard-shelled capsules), granules (including dry syrups), powder drugs (e.g. powders), fine granules, and pills; water based and non-water based oral administration solutions (including liquids, suspensions, syrups, etc.); and external preparations such as ointments, cataplasms, liniment, lotions, solutions for external application, dusting powders, creams, gels, emulsions, hair tonics, and hair sprays.

To produce the aforementioned various preparations, the sialooligosaccharide produced by the present invention is blended with additives that are usually acceptable in pharmaceutical products, quasi-drugs, health foods, or cosmetics and the blend is subjected to well-known methods. Examples of such additives include, but are not limited to excipients, lubricants (coating agents), binding agents, disintegrating agents, stabilizers, flavoring agents, bases, dispersants, diluents, surfactants, emulsifiers, transdermal absorption promoting agents, pH adjusting agents, preservatives, coloring agents, oils (e.g. oils and fats, mineral oils), moisturizing agents, alcohols, thickeners, polymers, film-forming agents, ultraviolet absorbers, cell activators, antioxidants, antiseptics, algefacients, deodorants, pigments, dyes, perfumes, sugars, amino acids, vitamins, organic acids, organic amines, plant extracts, etc.

EXAMPLES

Example 1

The Production of a Hydrolysate Containing Sialooligosaccharides
Method of Treatment with a Dilute Alkali A commercially available nest of a swiftlet (scientific name: *Aerodramus fuciphagus germani*) (10 g, obtained from a Chinese food store in Indonesia) was added to 1000 ml of a 0.25 wt. % potassium hydroxide aqueous solution, followed by grinding with a mixer. The resulting mixture was heated to 80° C. and kept at the same temperature for 40 minutes. After being cooled to 4° C., the mixture was subjected to centrifugation and filtration to remove insoluble matter. Salts and impurities were subsequently removed from the mixture by electrodialysis, and the resulting mixture was dried to recover a 3.33 g aliquot, which is hereinafter called the test substance 1.

Method of Treatment with an Acid

The technique of acid hydrolysis conventionally used to liberate sugars from glycoproteins was performed for comparison.

The same amount of swift's nest as described above was added to 1000 ml of 0.5 M hydrogen chloride, followed by grinding with a mixer. The resulting mixture was heated to 80 C.° and kept at the same temperature for 40 minutes. In accordance with the same procedure as described above, 0.81 g of a dry product was obtained, which is hereinafter called the test substance 2.

Analysis by Gel Filtration Chromatography

Each of the test substances 1 and 2 was dissolved in a 0.1 M phosphate buffer solution (pH 6.8) at a concentration of 1 mg/ml, and fractionation analysis was performed using gel filtration chromatography (GFC).

Conditions for GFC
Resin: TOYOPEARL® HW40S (produced by Tosoh Corporation) (Exclusion limit molecular weight<10,000 Da)
Column: Internal diameter 20 mm×Column length 950 mm (prepared by packing the above-noted resin into MM column produced by Yamazen Corporation (Internal diameter 20 mm×Length 1,000 mm) to cover a length of 950 mm)
Mobile phase: 0.1 M phosphate buffer (pH 6.8)
Injection: 1 ml (Loading amount: 1 mg) (an injector produced by ATTO was used)
Flow rate: 0.3 ml/minute (a pump produced by Lab-Quatec Corporation and having a model number of WORK-21, LP6300 was used)
Fractionation: 2 ml/tube (a fraction collector produced by Gilson Corporation and having a model number of FC203B was used)
Detection wavelength: 265 nm and 480 nm
Elution patterns by GFC are shown in FIG. 1.

Ultraviolet light absorption was measured at 265 nm for the samples fractionated in the individual tubes, and hexoses were measured by phenol-sulfuric acid method (absorption wavelength: 480 nm); as a result of measuring the absorption at 265 nm, multiple peaks were observed across several of the fractionated samples from the test substance 2 obtained by the treatment with hydrogen chloride, but no absorption was detected in the measurement of hexose, so hexoses in the sugar chains may have been degraded to pieces. On the other hand, in the measurement of hexoses for the test substance 1 obtained by the treatment with potassium hydroxide, absorption was observed in the samples fractionated in the $40^{th}$ to $42^{nd}$ tubes, and it appeared as a single peak (peak top molecular weight: about 2 kDa). These results suggest that the test substance 1 obtained by the treatment with potassium hydroxide in the present Example contains oligosaccharides having deduced molecular weights of 1.7 to 2.3 kDa.

Measurement of the Sialic Acid and Hexose Levels in the Test Substances

The sialic acid and hexose levels in the test substances were measured to verify that the oligosaccharides contained in the test substance 1 are sialooligosaccharides and that the test substance 2 does not contain any hexose.

Sialic acids were measured by direct Ehrlich's reaction (Course in Biochemical Experiments 4: Chemistry of Sugars (vol. 2 in two volumes), page 381, edited by the Japanese Biochemical Society, *Tokyo Kagaku Dojin,* 1976).

That is, 200 μl of a reagent prepared by dissolving p-dimethylaminobenzaldehyde (5 g) in 100 ml of a liquid mixture consisting of equal volumes of hydrogen chloride and water was added to 1 ml of each of the sample solutions; the resulting mixture was heated in a boiling water bath for 30 minutes and then cooled to room temperature under flowing water. The absorbance at 565 nm was subsequently measured.

Hexoses were measured by the phenol-sulfuric acid reaction (Course in Biochemical Experiments 4: Chemistry of Sugars (vol. 2 in two volumes), page 370, edited by the Japanese Biochemical Society, *Tokyo Kagaku Dojin,* 1976).

That is, 100 μl of a phenol reagent having a concentration of 5% by volume was added to 100 μl of each of the sample solutions, followed by thorough stirring. To the resulting mixture, 1 ml of sulfuric acid was added and after blending by thorough shaking, the absorbance at 480 nm was measured.

The results of measurements on the individual test substances for recovery rate, GFC elution pattern, as well as sialic acid and hexose levels and the results of measurements on the reference standard of sialic acid (N-acetylneuraminic acid produced by Wako Pure Chemical Industries, Ltd. and having a product number of 011-26173) for GFC elution pattern, as well as sialic acid and hexose levels are collectively shown in Table 1.

TABLE 1

| Test substance | Recovery rate (%) | GFC elution pattern | Sialic acid level (wt. %) | Hexose level (wt. %) | Sialic acid/hexose weight ratio |
|---|---|---|---|---|---|
| Test Substance 1 | 33.3 | Single peak | 36.0 | 51.0 | 0.7 |
| Test Substance 2 | 8.1 | Multiple peaks | 0.5 | Trace amount | Calculation impossible |
| Reference Standard of sialic acid* | — | Single peak | 100 | Not detected | — |

*N-acetylneuraminic acid ($C_{11}H_{19}NO_9$)

The test substance 1 was shown to comprise 36 wt. % sialic acids and 51 wt. % hexoses, thus verifying that the oligosaccharides contained in the test substance 1 were sialooligosaccharides. Furthermore, the sialic acid/hexose weight ratio was calculated to be 0.7.

On the other hand, although the test substance 2 was shown to comprise 0.5 wt. % sialic acids, it was shown to contain only a trace amount of hexoses, thus verifying substantial absence of hexoses.

Example 2

Tests for Evaluating the Ability of the Test Substances to Promote the Production of Insulin-Like Growth Factor-1 (IGF-1)

Each of the test substances produced in Example 1 and the reference standard of sialic acid (N-acetylneuraminic acid produced by Wako Pure Chemical Industries, Ltd. and having a product number of 011-26173) was dissolved in drinking water, and after adjustment of their concentrations, the individual solutions were administered to mice (n=5); the test substances were administered at 5 mg/kg weight/day.

After rearing for 3 weeks, the concentration of IGF-1 in peripheral blood was examined by ELISA method. The results are shown in Table 2.

TABLE 2

The results of evaluating the ability of the test substances to promote the production of IGF-1

| Test Substance | IGF-1 (μg/ml) |
|---|---|
| Test Substance 1 | 6.3 |
| Test Substance 2 | 0.28 |
| Reference Standard of sialic acid* | 4.4 |
| Control (untreated) | 0.03 |

*N-acetylneuraminic acid ($C_{11}H_{19}NO_9$)

As with the reference standard of sialic acid, the sialooligosaccharide-containing hydrolysate of the test substance 1 obtained by the treatment with potassium hydroxide promoted the production of IGF-1 in mice upon oral administration. The reference standard of sialic acid and the test substance 1 were compared for the ability to promote the production of IGF-1; as shown in Table 2, the administration of the reference standard of sialic acid gave an IGF-1 concentration of 4.4 μg/ml whereas the administration of the test substance 1 gave an IGF-1 concentration of 6.3 μg/ml, so the test substance 1 was approximately 43% higher in the ability to promote the production of IGF-1.

Example 3

Tests for Evaluating the Cell-Proliferative Activity of the Test Substance 1

NIH3T3 cells were cultured in a 96-well microplate to give a cell density of $10^5$ cells/well, and solutions of concentration-adjusted test substance 1 and reference standard of sialic acid (N-acetylneuraminic acid produced by Wako Pure Chemical Industries, Ltd. and having a product number of 011-26173) were each added in an amount of 10 μl, followed by culture in a $CO_2$ incubator for 24 hours (37° C., 4.5% $CO_2$). Cell proliferation was measured by the MTT assay method using a kit (Cell Counting Kit-8 produced by DOJINDO Corporation and having a product number of 347-07621). The results are shown in Table 3.

TABLE 3

The results of evaluating the cell-proliferative activity of the test substance 1

| | Additive concentration (mg/ml) | | | | | | |
|---|---|---|---|---|---|---|---|
| | 0 | 0.08 | 0.31 | 1.25 | 2.5 | 5.0 | 10.0 |
| Test substance 1 | 100 | 103 | 111 | 115 | 113 | 121 | 120 |
| Reference standard of sialic acid* | 100 | 96 | 98 | 101 | 98 | 99 | 102 |

*N-acetylneuraminic acid ($C_{11}H_{19}NO_9$)

The cell proliferation rate was calculated at the respective additive concentrations of the test substance 1, with the value for no addition (0 mg/ml) of the test substance 1 being taken as 100.

The cell proliferation rate was calculated at the respective additive concentrations of the reference standard of sialic acid, with the value for no addition (0 mg/ml) of the reference standard of sialic acid being taken as 100.

No change was recognized in the proliferation rate even when the reference standard of sialic acid was added at a concentration of 10.0 mg/ml whereas the test substance 1, as shown in Table 3, allowed the cell proliferation rate to increase in a concentration-dependent manner and reached a plateau when the additive concentration thereof was 5.0 mg/ml or higher.

Example 4

Tests for Evaluating the Effects of the Test Substance 1 in Volunteer Subjects

1. The Skin Care Effect

Figure 2:
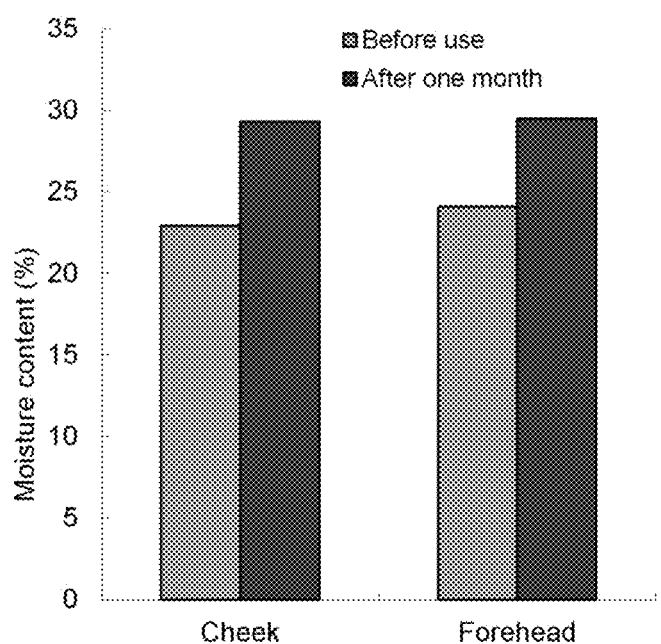
FIG. 2 gives bar charts showing changes in the moisture content of skin due to the use of a lotion containing the test substance 1. The moisture content (wt. %) measured before use and after use for one month is shown for both cheek (left chart) and forehead (right chart).

A lotion was prepared by dissolving the test substance 1 in deionized water to give a concentration of 0.5 wt. %, and 10 volunteer subjects aged 50 or older (5 males, 5 females) were asked to use said lotion for evaluating its effect. To estimate the moisture content of the skin, the moisture contents in cheek and forehead before face washing in the morning were measured with digital moisture checker 1175 (produced by WORLDJB CO., LTD.). The results are shown in FIG. 2.

By using the above-described lotion containing the test substance 1 for a month, the moisture contents in cheek and forehead increased from 22.9 wt. % to 29.3 wt. % and from 24.1 wt. % to 29.5 wt. %, respectively.

Furthermore, the effect of the lotion on skin condition was evaluated based on the subjective opinion of each volunteer subject. The results are shown in Table 4.

TABLE 4

The evaluation of the effect of the lotion containing the test substance 1 on skin condition

| Evaluation | Exacerbated | No change | Improved | Greatly improved | Total number of subjects |
|---|---|---|---|---|---|
| Number of subjects | Male: 1 Female: 0 | Male: 0 Female: 1 | Male: 3 Female: 2 | Male: 1 Female: 2 | Male: 5 Female: 5 |

Among the 10 volunteer subjects, 8 in total consisting of 4 males and 4 females (80% of the total) responded that their skin conditions were improved or greatly improved by the use of the lotion containing the test substance 1. Furthermore, the 8 volunteer subjects who responded that they had an improvement or great improvement in their skin conditions were asked to tell the specific improvements and 4 out of the 8 respondents referred to "moistness" and 4 referred to "smooth feeling."

2. The Effect of Improving Sarcopenia

A test food was prepared by compounding 0.5 wt. % of the test substance 1 with whey protein (WPC, or Whey Protein Concentration; product of Kyodo Milk Industry Co., Ltd.), and a total of 30 volunteer subjects consisting of males and females in their 60s to 80s who were prone to stumble and had slight difficulty in walking, who had slight-to-moderate disabilities in their knees, shoulders, waist, etc., and who were suffering from incurable peripheral numbness of unknown cause in their hands and lower extremities (each of these symptoms was self-reported) were defined as subjects who presented with symptoms of sarcopenia, and were asked to ingest the test food at a daily dose of 5 g/day (1 pack) for one month. The method and time for the ingestion of the test food were not limited in any way, and the subjects were not informed at all of the mechanism of action or objective of the test food. These were the measures for minimizing the placebo effect. After the passage of one month, any changes that occurred were evaluated on a 4-point scale. The results are shown in Table 5.

TABLE 5

The evaluation of the effects of the test food on symptoms of sarcopenia

| Evaluation | Exacerbated | No change | Improved | Greatly improved | Total number of subjects |
|---|---|---|---|---|---|
| Number of subjects | Male: 0 Female: 1 | Male: 1 Female: 1 | Male: 9 Female: 7 | Male: 6 Female: 5 | Male: 16 Female: 14 |

Among the total 30 subjects, 27 in total consisting of 15 males and 12 females (90% of the total) responded that their symptoms of sarcopenia were improved or greatly improved.

Table 6 lists comments (multiple responses allowed) that were common in those 27 subjects (15 males, 12 females) who responded that their symptoms were improved or greatly improved.

TABLE 6

Comments on the improvements of symptoms of sarcopenia by the test food

| Comments | Number of male subjects | Number of female subjects |
|---|---|---|
| Walking became easy | 11 | 10 |
| No stumbles occurred | 9 | 8 |
| Standing up from and sitting down on chair became easy | 8 | 6 |
| Taking a break became unnecessary during walking | 6 | 4 |
| Pain and fatigue in various joints or muscles became unfelt | 5 | 4 |
| Waking with quick steps became possible | 5 | 3 |
| Waist and hip have become toned up | 3 | 8 |

3. The Effect of Improving Sparse Hair, Hair Loss, Etc.

An aqueous solution containing 0.05 wt. % of the test substance 1 and 0.01 wt. % of fucoidan which is one of sulfated polysaccharides was applied in an appropriate amount as a test solution to 7 male subjects (who were suffering from sparse hair or hair loss) by themselves after hair washing at night. After the passage of a month, any changes that occurred were evaluated on a 4-point scale. The results are shown in Table 7.

TABLE 7

The evaluation of the effect of the test solution on sparse hair, hair loss, etc.

| Evaluation | Exacerbated | No change | Improved | Greatly improved | Total number of subjects |
|---|---|---|---|---|---|
| Number of subjects | 0 | 1 | 5 | 1 | 7 |

Six out of the 7 subjects (i.e. 85% or more of the total) responded that their conditions were improved or greatly improved.

Table 8 lists comments (multiple responses allowed) that were common in those 6 subjects who felt that their conditions of sparse hair, hair loss, etc. were improved or greatly improved.

TABLE 8

Comments on the improvements of sparse hair, hair loss, etc. by the test solution

| Comments | Number of male subjects |
|---|---|
| Hair loss was dramatically decreased | 5 |
| Gray hair became less noticeable | 2 |
| The speed of hair growth was increased | 4 |

What is claimed is:

1. A method of producing a sialooligosaccharide, which comprises:

(1) hydrolyzing a sialoglycoprotein in an alkaline aqueous solution consisting essentially of an alkali by heating at a temperature from 70 to 90° C. in the alkaline aqueous solution; and (2) purifying the hydrolysate to obtain the sialooligosaccharide, wherein a weight ratio of sialic acid to hexose contained in the resulting sialooligosaccharide is from 0.5 to 0.9; and wherein the sialoglycoprotein is a mucin-type glycoprotein contained in the nest of the Collocaliini tribe.

2. The method according to claim 1, wherein the alkaline aqueous solution is an aqueous solution of potassium hydroxide.

3. The method according to claim 1, wherein the purification is performed by reverse osmosis membrane filtration or electrodialysis.

4. The method according to claim 1, wherein the concentration of the alkali in the alkaline aqueous solution is from 0.2 to 0.5 wt. %.

* * * * *